United States Patent [19]

Brenner et al.

[11] 3,937,740

[45] Feb. 10, 1976

[54] PROCESS FOR THE MANUFACTURE OF 2,3,6-TRIMETHYLPHENOL

[75] Inventors: Wolf Brenner, Fullinsdorf; Herbert Lindlar, Reinach; Rudolf Hinderling, Riehen, all of Switzerland

[73] Assignee: Hoffmann-La Roche Inc., Nutley, N.J.

[22] Filed: Mar. 28, 1974

[21] Appl. No.: 455,821

[30] Foreign Application Priority Data

Apr. 5, 1973  Switzerland.......................... 4918/73

[52] U.S. Cl............ 260/621 R; 252/457; 260/624 C
[51] Int. Cl.$^2$........................................ C07C 39/06
[58] Field of Search......... 260/621 R, 624 C, 624 R

[56] References Cited
UNITED STATES PATENTS

| 2,448,942 | 9/1948 | Winkler........................... 260/624 C |
| 3,716,589 | 2/1973 | Kotangawa et al............. 260/624 C |

FOREIGN PATENTS OR APPLICATIONS

| 717,588 | 10/1954 | United Kingdom............. 260/621 R |
| 2,127,083 | 6/1971 | Germany.......................... 260/621 R |

*Primary Examiner*—James O. Thomas, Jr.
*Assistant Examiner*—W. B. Lone
*Attorney, Agent, or Firm*—Samuel L. Welt; Jon S. Saxe; Richard A. Gaither

[57] ABSTRACT

A process for producing 2,3,6-trimethylphenol by reacting a m-cresol with methanol in the gas phase in the presence of a catalyst containing ceric oxide, zinc oxide, and an oxide of a metal selected from the group consisting of an alkali metal, barium, calcium or strontium.

6 Claims, No Drawings

PROCESS FOR THE MANUFACTURE OF 2,3,6-TRIMETHYLPHENOL

BACKGROUND OF THE INVENTION

In the past 2,3,6-trimethylphenol has been manufactured from the reaction of m-cresol with methanol utilizing various catalyst systems such as described in DAS 1,263,010, Mar. 14, 1968; DAS 1,269,125, May 5, 1968; Japanese Patent Publication 37,942/72, Sept. 25, 1972; and DAS 2,124,901, Dec. 16, 1971. Such known processes for the manufacture of 2,3,6-trimethylphenol in which catalyst systems of various types are used, generally have the disadvantage that the yields of the desired products are relatively small. Furthermore, the catalysts used generally have a relatively short life.

SUMMARY OF THE INVENTION

In accordance with this invention, it has been found that 2,3,6-trimethylphenol can be produced in high yields by the reaction of m-cresol and methanol where the methanol and m-cresol is present in the gas phase in a catalyst system containing 24 parts by weight of said system of magnesium in the form of magnesium oxide, 2 to 15 parts by weight of said system of cerium in the form of ceric oxide; 1 to 5 parts by weight of said system of zinc in the form of zinc oxide and 0.1 to 1.5 parts by weight of said system of a metal selected from the group consisting of an alkali metal, barium, calcium, or strontium, in the form of its oxide. By use of this catalyst system the 2,3,6-trimethylphenol is produced from m-cresol in very high yields, i.e., in yields of 90% or higher. Furthermore, these catalysts have a very long life since they can be used for more than 1200 hours or longer without any noticeable loss of activity being observed.

DETAILED DESCRIPTION OF THE INVENTION

The catalyst system for use in this invention contains 24 parts by weight of magnesium in the form of magnesium oxide, 2 to 15 parts by weight of said system of cerium in the form of ceric oxide, 1 to 5 parts by weight of said system of zinc in the form of zinc oxide and 0.1 to 1.5 parts by weight of said system of an alkali metal, barium, calcium or strontium in the form of the corresponding oxides. This catalyst system can, if desired, contain inert ingredients. The parts by weight refer in each case to the weight of the respective metal.

The term "alkali metal" as used in this specification includes any one of the alkali metals such as lithium, sodium, potassium, rubidum and caesium. The preferred alkali metals are sodium and potassium, especially sodium.

A preferred embodiment of the present process consists in using a catalyst system which contains 24 parts by weight of said system of magnesium, 5 to 8 parts by weight of said system of cerium, 1 to 2 parts by weight of said system of zinc and 0.1 to 0.5 parts by weight of said system of metal selected from the group consisting of alkali metal, barium, calcium or strontium, in each case in the form of the corresponding oxides.

The reaction, which is carried out with the methanol and m-cresol in the gas phase, can be carried out within a wide temperature range, namely within a range of from about 300°C. to about 520°C. It is preferred to carry out this reaction at a temperature between about 390°C. to about 450°C., especially between about 410°C. to about 440°C.

The reaction can be carried out at a pressure ranging from normal pressure, i.e., 1 atmospheres 10 10 atmospheres. The reaction is preferably carried out at a pressure ranging from normal pressure (1 atmosphere) to about 3 atmospheres.

The molar ratio of methanol to m-cresol can be between about 2:1 and about 20:1. The reaction is preferably carried out using a molar ratio of methanol to m-cresol of between about 5:1 and about 15:1.

The reaction mixture obtained after carrying out the process consists essentially of the desired product, namely 2,3,6-trimethylphenol, and, in addition, small amounts of 2,3,4,6-tetramethylphenol, small amounts of the m-cresol starting material, o-cresol, 2,6-xylenol, phenol, 2,5-xylenol, 2,3-xylenol, 2,4,6-trimethylphenol and 2,3,5-trimethylphenol. This reaction mixture can be used without further purification, for example for the manufacture of trimethylquinone. On the other hand the 2,3,6-trimethylphenol can be recovered from the reaction mixture by conventional means, e.g. by distillation.

The present invention is also concerned with a catalyst suitable for carrying out the foregoing process, said catalyst containing 24 parts by weight of magnesium in the form of magnesium oxide, 2 to 15 parts by weight of cerium in the form of ceric oxide, 1 to 5 parts by weight of zinc in the form of zinc oxide and 0.1 to 1.5 parts by weight of an alkali metal, barium, calcium or strontium in the form of the corresponding oxides.

A particularly preferred catalyst contains 24 parts by weight of magnesium, 5 to 8 parts by weight of cerium, 1 to 2 parts by weight of zinc and 0.1 to 0.5 parts by weight of an alkali metal, barium, calcium or strontium, in each case in the form of the corresponding oxides.

A catalyst as hereinbefore defined can be prepared, also in accordance with the present invention, by treating magnesium carbonate or magnesium oxide with a solution or suspension of a cerium compound, a zinc compound and a metal compound where said metal is an alkali metal, barium, calcium or strontium, drying the product obtained and heating the dried product to about 400°C. to about 600°C.; said compounds being used in such amounts that the catalyst obtained after heating corresponds to the quantitative proportions given hereinbefore.

In this process there is preferably used as the cerium compound a cerium salt containing a readily volatile anion. especially cerium (III) nitrate. Zinc oxide is preferably used as the zinc compound.

The corresponding oxides, hydroxides or carbonates can be used as the alkali metal, barium, calcium or strontium compound.

The suspension or solution, which contains the metal compound, the zinc compound and the cerium compound is formed by dissolving or suspending the metal compound, the zinc compound and the cerium compound is an inert solvent. For use in preparing these suspensions or solutions any conventional inert solvent such as water, lower alkanols, such as methanol and ethanol, etc. can be utilized. The resulting solution or suspension is then added to the magnesium carbonate or magnesium oxide to form a mixture. In the next step of forming the catalyst system, the mixture is dried to remove the solvent. Any conventional method of removing the solvent can be utilized in carrying out this procedure. In the final step of this process, the dried mixture is heated to 400°C. to 600°C. whereupon the catalyst system for use in this invention forms.

The following examples are illustrative but not limitative of the present invention.

EXAMPLE 1

570 ml. of the catalyst prepared according to Example 2 hereinafter are placed in a cylindrical (diameter of 24.5 cm) reactor which is connected with a storage vessel and is provided with a metering pump for transmitting the starting material to the reactor. The reactor is electrically heated externally.

A mixture of m-cresol and methanol is a molar ratio of 1:10 is conducted at 450°C. through the reactor containing the catalyst, i.e., with a velocity of 50 g. of mixture/hour The reaction mixture containing the desired 2,3,6-trimethylphenol is led off at the lower end of the reactor.

EXAMPLE 2

The catalyst used in Example 1 was prepared as follows:

110 g. of magnesite (particle size 2–4 mm.) were saturated in the flask of a rotary evaporator at 60°C. with a solution of 204.5g of cerium (III) nitrate $6H_2O$ in 500 g. of methanol and thereupon freed from the methanol under reduced pressure. To the still slightly moist mixture were added, with mixing, 27.4 g. of zinc oxide and 5 g. of sodium carbonate.

The thus-obtained mixture was spread out on a flat base and the methanol still present was burnt. In so doing, a partial decomposition of the cerium nitrate takes place with evolution of nitrous gases. The majority of the nitrous gases are expelled by slow heating for 3 hours at 500°C. in an electric muffle oven. After separation of the catalyst powder by sieving, the catalyst (24 parts by weight of magnesium, 6 parts by weight of cerium, 2 parts by weight of zinc and 0.2 parts by weight of sodium, in each case in the form of the corresponding oxides) is gassed in the reactor described in Example 1 for 3 hours at 450°C. with an inert gas (e.g. nitrogen) and then with methanol vapor. The thus-treated catalyst is ready for use in the reaction described in Example 1.

EXAMPLE 3

The reaction described in Example 1 was carried out using other catalysts prepared in an analogous manner to that described in Example 2. These catalysts (a) – (f) contained metal oxides in the following amounts with respect to the corresponding metals:

|    | Mg | Ce | Zn | Li  | Na  | K   | Ca  | Ba  |
|----|----|----|----|-----|-----|-----|-----|-----|
| a) | 24 | 6  | 2  | 0.2 | —   | —   | —   | —   |
| b) | 24 | 6  | 2  | 1.0 | —   | —   | —   | —   |
| c) | 24 | 6  | 2  | —   | 0.2 | —   | —   | —   |
| d) | 24 | 6  | 2  | —   | —   | 0.2 | —   | —   |
| e) | 24 | 6  | 2  | —   | —   | —   | 0.2 | —   |
| f) | 24 | 6  | 2  | —   | —   | —   | —   | 0.2 |

We claim:

1. A process for producing 2,3,6-trimethylphenol comprising reacting m-cresol with methanol wherein the m-cresol and methanol are present in the gas phase, said reaction taking place in the presence of a catalyst system composed of 24 parts by weight of said catalyst system of magnesium in the form of magnesium oxide, 2 to 15 parts by weight of said catalyst system cerium in the form of ceric oxide, 1 to 5 parts by weight of said system of zinc in the form of zinc oxide and 0.1 to 1.5 parts by weight of said system of metal selected from the group consisting of an alkali metal, barium, calcium or strontium wherein said metal is in the form of its oxide wherein the reaction is carried out at a temperature of from about 300°C and about 520°C and at a pressure of from 1 atmosphere to about 10 atmosphere.

2. A process of claim 1 wherein the catalyst system contains 24 parts by weight of magnesium; 5 to 8 parts by weight of cerium in the form of ceric oxide; 1 to 2 parts by weight of zinc in the form of zinc oxide and 0.1 to 0.5 parts by weight of said metal in the form of the metal oxide.

3. A process of claim 1 wherein the reaction is carried out at a temperature of from about 300°C. and about 450°C.

4. A process of claim 1 wherein methanol and m-cresol are present in the reaction in a molar ratio of from about 2:1 to about 20:1.

5. A process of claim 4 wherein methanol and m-cresol are present in the reaction in a molar ratio of from about 5:1 to about 15:1.

6. A process of claim 1 wherein the reaction is carried out at a pressure of from 1 atmosphere to about 3 atmospheres.

* * * * *